United States Patent [19]

Murphy et al.

[11] 4,012,525
[45] Mar. 15, 1977

[54] NOVEL PROPOXYPHENE DOSAGE REGIMEN

[75] Inventors: Patrick J. Murphy; Rodney C. Nickander, both of Indianapolis, Ind.

[73] Assignee: Eli Lilly and Company, Indianapolis, Ind.

[22] Filed: Oct. 10, 1975

[21] Appl. No.: 621,263

[52] U.S. Cl. .............................................. 424/311
[51] Int. Cl.$^2$ ...................................... A61K 31/22
[58] Field of Search ................................... 424/311

[56] References Cited

OTHER PUBLICATIONS

Cooper et al.—Chem. Abst., vol. 82 (1975) p. 93155k.

*Primary Examiner*—Sam Rosen
*Attorney, Agent, or Firm*—James L. Rowe; Everet F. Smith

[57] ABSTRACT

Initial oral administration of an l-propoxyphene loading dose with a lowered d-proxyphene dose enhances analgesic activity of d-propoxyphene.

2 Claims, No Drawings

NOVEL PROPOXYPHENE DOSAGE REGIMEN

BACKGROUND OF THE INVENTION

Propoxyphene hydrochloride, named in the U.S. Pharmacopeia XVIII, page 556 as (+)-α-4-(dimethylamino)-3-methyl-1,2-diphenyl-2-butanol propionate hydrochloride or by Poland and Sullivan, *J. Am. Chem. Soc.*, 77, 3400 (1955) as α-d-4-dimethylamino-1,2-diphenyl-3-methyl-2-propionyloxybutane hydrochloride, has been marketed for many years as a potent analgesic of low physical dependance liability. The corresponding racemate, α-dl-4-dimethylamino-1,2-diphenyl-3-methyl-2-propionyloxybutane, was prepared by Poland and Sullivan, *J. Am. Chem. Soc.*, 75, 4458 (1953). Pharmacology of the racemate was reported by Robbins, *J. Am. Pharm. Soc.*, 44 497 (1955) who determined that, by the subcutaneous route, the analgesic dosage of the racemate was in the range 10–20 mg./kg. Generally, the analgesic potency of the racemate was taken to be equal to about half that of codeine. Miller et al., *J. Pharm. Sci.*, 52, 446 (1963) reported on both the analgesic and antitussive potency by parenteral administration for the racemic compound as well as other closely related derivatives. It was reported by Poland and Sullivan, *J. Am. Chem. Soc.*, 77, 3400 (1955), however, that the pure α-d-isomer-(+)-d-4-dimethylamino-1,2-diphenyl-2-butanol propionate was responsible for the analgesic activity of the α-dl-mixture in that 10 mg/kg. of the α-d-isomer produced an analgesic effect equal to that of 20 mg/kg. of the racemate when administered subcutaneously. They also reported that the α-l-isomer gave no response with subcutaneous doses from 10 to 80 mg./kg. Gruber, *J. Lab. Clin. Med.* 44, 805 (1954) reported on the administration of the racemate, named by him 1,2-diphenyl-2-propionoxy-3-methyl-4-dimethylaminobutane hydrochloride, in humans by the oral route. It was his conclusion that 80 mg. of the racemate was equivalent to 325 mg. of aspirin and 50 mg. was equivalent to 32.5 mg. of codeine phosphate. Currently, propoxyphene hydrochloride (the pure d-isomer) is sold in single dosage forms containing 32 or 65 mg. of drug. Codeine sulfate is currently marketed in 15, 30 and 60 mg. tablets.

Cooper and Anders, reporting in *Life Sciences*, 15, 1665 (November, 1974), stated that administration subcutaneously to mice of 100 or 200 micromoles per kg. of levo-propoxyphene produced primarily an intensification of the analgesic effect of the dextro-enantiomer also administered subcutaneously. It was also reported on Apr. 15, 1975, at the annual meeting of the Federated American Society for Experimental Biologists, Atlantic City, N.J., by Murphy et al. that coadministration of equal amounts of l-propoxyphene with a d-propoxyphene dose of 10 mg./kg. orally resulted in increased circulating plasma levels of d-propoxyphene 15 minutes after administration and that the administration of l-propoxyphene also enhanced the analgesic activity of d-propoxyphene. (Murphy et al. were using the name d-propoxyphene as a synonym for propoxyphene as used in the U.S. Pharmacopeia in order to differentiate it from l-propoxyphene which is the U.S. Pharmacopeia name for this compound, marketed as an antitussive as the napsylate salt), Murphy et al. further reported that the combination of d- and l-propoxyphene at 10 mg./kg. of each enantiomorph was found to have activity equivalent to that observed with d-propoxyphene alone at a 20 mg/kg. dose orally. In each instance, maximum analgesic effects were observed 15 minutes after administration of both drugs by the oral route.

DESCRIPTION OF THE INVENTION

This invention provides a method for enhancing the analgesic action of (+)-d-4-dimethylamino-1,2-diphenyl-3-methyl-2-butanol propionate (to be referred to hereinafter as d-propoxyphene) in mammals by administering from 10 to 20 mg. of (−)-l-4-dimethylamino-1,2-diphenyl-3-methyl-2-butanol propionate (to be referred to hereinafter as l-propoxyphene) concomitantly with each 5 mg. dose of d-propoxyphene or from 5 to 10 mgs. of l-propoxyphene concomitantly with each 10 mg. dose of d-propoxyphene, administered in capsules, each capsule containing the predetermined dose of d-propoxyphene or of l-propoxyphene plus other excipients, diluents and the like to make up a final volume of 100 to 500 mg. of pharmaceutical formulation per capsule, depending on the size of the capsule. The dosage forms employed can be those presently being used for the administration of either d-propoxyphene or of l-propoxyphene separately. The dosage rate can thus be adjusted by administering one or two 60 mg. capsules of l-propoxyphene free base for each 32 to 65 mg. capsule of d-propoxyphene hydrochloride. Other dosage regimens containing small amounts of l-propoxyphene require special dosage forms not currently available.

Both d-propoxyphene and l-propoxyphene are preferably administered as pharmaceutically-acceptable acid addition salts. Pharmaceutically-acceptable salts of d- or l-propoxyphene include salts derived from inorganic acids such as: hydrochloric acid, nitric acid, phosphoric acid, sulfuric acid, hydrobromic acid, hydriodic acid, nitrous acid, phosphorous acid and the like, as well as salts derived from non-toxic organic acids such as aliphatic mono and dicarboxylic acids, etc. Such pharmaceutically-acceptable salts thus include the sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate (napsylate) and the like salts. Preferred salts are the hydrochloride and the napsylate. In addition, either drug can be administered in the form of a solution or suspension or in the form of tablets. A pharmaceutically-acceptable suspension form of l-propoxyphene napsylate is currently available commercially and d-propoxyphene can readily be substituted for l-propoxyphene in such a suspension. Tablets containing either of the two drugs can be prepared according to methods well known in the art. As is commonly done with tablets, each tablet can be scored so as to provide half and quarter dosages.

Typically, our novel process can be carried out as follows:

A mammal in pain and requiring analgesia is given at appropriate intervals during the initial treatment period one 32 mg. capsule of d-propoxyphene hydrochloride and a loading dose consisting of one capsule containing 60 mg. of l-propoxyphene free base equivalent, in salt form. After the initial loading period, the dosage of d-propoxyphene hydrochloride is maintained at the 32 mg. level but l-propoxyphene need no longer be given. This dosage regimen initially is the full equivalent of a dosage regimen requiring 65 mg. doses of d-propoxyphene by itself. With humans, the analgesic doses would be given at 6 hour intervals.

The effect of the initial loading dose of l-propoxyphene wears off in time as evidenced by an unsatisfactory level of analgesia in the subject; at this point, therefore, there will be an increased need for higher d-propoxyphene levels in order to attain the same degree of analgesia as under the above-described regimen. At this point in time, therefore, the dosage schedule will revert to the original dosage utilizing a loading dose of l-propoxyphene with the lower d-propoxyphene dosage during the initial period until satisfactory analgesia brought about by increased d-propoxyphene levels is attained. Alternatively, the dose level of d-propoxyphene can be increased.

Alternatively, α-dl-4-dimethylamino-1,2-diphenyl-3-methyl-4-propionoxy butane, the racemate containing equal quantities of d-propoxyphene and l-propoxyphene, can be administered during the initial period during which analgesia is required, followed by continuing administration with the same lower d-propoxyphene dose. For example, employing production of analgesia in human subjects, a capsule containing 65 mg. of the racemate as the hydrochloride salt can be administered at 6 hour intervals for the first 6–24 hour period followed by administration of 32 mg. capsules of d-propoxyphene hydrochloride four times a day until a higher degree of analgesia is required, at which time the regimen can be repeated. If, in the individual case, the equal amount of l-propoxyphene (in milligrams) is not sufficient to provide the desired analgesic enhancement, an added quantity of l-propoxyphene can be administered alone as in a separate capsule.

Alternatively, the entire mixture can be prepared using the racemate plus an added quantity of the l-propoxyphene in a single dosage form with a pre-determined ratio of d- to l-propoxyphene therein. The same or different acid addition salts can be used.

The process of this invention is further illustrated by the following specific examples in which d-propoxyphene, l-propoxyphene and combinations thereof were administered to rats by the oral route and the degree of analgesic activity produced thereby measured by a standard assay procedure for analgesia, the rat tail jerk method. In these experiments, varying doses of d-propoxyphene by itself or l-propoxyphene by itself were given to groups of five rats and the increase, if any, in reaction time measured at 15 minutes and one-half hour intervals after administration of the analgesic dose. Similarly, combination of d- and l-propoxyphene were also administered to groups of five rats each and the difference in reaction time measured. The increase, if any, in reaction time caused by the combination of d- and l-propoxyphene over the increase in reaction time produced by d-propoxyphene alone was subjected to statistical analysis and these analyses are also presented. The Student "Test for Statistical Significance" was employed with the probability being given as a p value.

The results of these experiments are given in Tables 1 and 2 below. In Table 1, the increase in reaction time attributable to administration of d- or l-propoxyphene as the hydrochloride salts alone or in combination at different dosage levels is given. In Table 2, the increase in reaction time (column 1) from Table 1 for a given dosage combination of d- and l-propoxyphene is compared directly (column 2) with the increase in reaction time for the same amount of d-propoxyphene as in the combination and the difference, showing enhanced analgesia, is subjected to statistical analysis.

TABLE 1

| Dosage In Mg./Kg. | | Time of Measurement After Administration in Min. | Reaction time ± in Secs SE | Diff. from Control | "p" Value |
|---|---|---|---|---|---|
| d-propoxyphene | l-propoxyphene | | | | |
| 10 | — | 15 | 7.35 ± .31 | + .25 | <.5 |
| 20 | — | 15 | 10.40 ± .74 | +3.30 | <.01 |
| 20 | — | 30 | 8.85 ± .15 | +1.75 | <.001 |
| 40 | — | 15 | 14.85 ± .15 | +7.75 | <.001 |
| — | 20 | 15 | 7.20 ± .20 | + .10 | >.5 |
| — | 20 | 30 | 7.0 ± .19 | − .10 | >.5 |
| 5 | 5 | 15 | 8.65 ± .57 | +1.55 | <.05 |
| 10 | 10 | 15 | 10.0 ± .44 | +2.90 | <.001 |
| 20 | 20 | 15 | 15.0 ± .00 | +7.90 | <.001 |
| 20 | 20 | 30 | 14.60 ± .40 | +7.50 | <.001 |
| Control | | 30 | 7.10 ± .13 | — | — |
| 5 | — | 15 | 7.20 ± .12 | − .05 | >.5 |
| 10 | — | 15 | 8.10 ± .40 | + .85 | <.2 |
| 5 | 5 | 15 | 7.95 ± .78 | + .70 | <.5 |
| 5 | 10 | 15 | 12.60 ±1.02 | +5.35 | <.001 |
| 5 | 20 | 15 | 13.15 ± .97 | +5.90 | <.001 |
| 10 | 1 | 15 | 7.65 ± .32 | + .40 | <.4 |
| 10 | 2 | 15 | 7.90 ± .26 | +.65 | <.1 |
| 10 | 5 | 15 | 11.20 ± .94 | +3.95 | <.01 |
| Control | | 15 | 7.25 ± .22 | — | — |

TABLE 2

| Dosage in Mg./Kg. | | | Time of Measurement After Administration in Min. | Diff. In Reaction Time | |
|---|---|---|---|---|---|
| d-propoxyphene l-propoxyphene Combination | | d-propoxyphene Alone | | in Secs. | "p" Value |
| 20 | 20 | 20 | 15 | 4.60 | <.001 |
| 20 | 20 | 20 | 30 | 5.75 | <.001 |
| 10 | 10 | 10 | 15 | 2.65 | <.01 |

TABLE 2-continued

| Dosage in Mg./Kg. | | | Time of Measurement After Administration in Min. | Diff. In Reaction Time | |
|---|---|---|---|---|---|
| d-propoxyphene Combination | l-propoxyphene | d-propoxyphene Alone | | in Secs. | "p" Value |
| 5 | 5 | 5 | 15 | .75 | <.4 |
| 5 | 10 | 5 | 15 | 5.40 | <.001 |
| 5 | 20 | 5 | 15 | 5.95 | <.001 |
| 10 | 1 | 10 | 15 | − .45 | <.5 |
| 10 | 2 | 10 | 15 | − .20 | >.5 |
| 10 | 5 | 10 | 15 | 3.10 | <.02 |

From Table 2, it can be seen that at least a 10 mg. dose of d-propoxyphene as the hydrochloride is needed to produce analgesia, but that a 5 mg. dose of d-propoxyphene hydrochloride administered in conjunction with a 10–20 mg. dose of l-propoxyphene hydrochloride yields a statistically significant increase in analgesia. With a 10 mg. dose of d-propoxyphene hydrochloride, however, a dose of l-propoxyphenyl hydrochloride as low as 5 mg. administered concomitantly produces increased analgesia.

We claim:

1. The method of enhancing the analgesia produced in mammals by oral administration thereto of d-propoxyphene or a pharmaceutically-acceptable salt thereof which comprises administering during the initial period during which it is desired to produce analgesia, a loading dose of from 10–20 mg. of l-propoxyphene free base equivalent for each 5 mg. dose of d-propoxyphene free base equivalent administered or from 5–10 mg. of l-propoxyphene free base equivalent for each 10 mg. dose of d-propoxyphene free base equivalent administered and then continuing administration of d-propoxyphene alone at the same dose level as in the initial period.

2. The method of enhancing the analgesia produced in mammals by oral administration thereto of d-propoxyphene or a pharmaceutically-acceptable salt thereof which comprises administering during the initial period during which it is desired to produce analgesia, a loading dose of from 10–20 mg. of l-propoxyphene free base equivalent for each 5 mg. dose of d-propoxyphene free base equivalent administered or from 5–10 mg. of l-propoxyphene free base equivalent for each 10 mg. dose of d-propoxyphene free base equivalent administered and then continuing administration of d-propoxyphene alone at the same dose level as in the initial period until the degree of analgesia produced thereby is no longer satisfactory and then repeating the concomitant administration of an l-propoxyphene loading dose as in the initial period while continuing the d-propoxyphene dosage.

* * * * *

UNITED STATES PATENT AND TRADEMARK OFFICE
CERTIFICATE OF CORRECTION

PATENT NO. : 4,012,525
DATED : March 15, 1977
INVENTOR(S) : Patrick J. Murphy, et al.

It is certified that error appears in the above-identified patent and that said Letters Patent are hereby corrected as shown below:

In Table 1, 18th line down from the top, starting with the second column, with the number "2", all columns should be shifted once to the left so that the columns are correctly aligned.

Signed and Sealed this

Seventh Day of June 1977

[SEAL]

Attest:

RUTH C. MASON
Attesting Officer

C. MARSHALL DANN
Commissioner of Patents and Trademarks